United States Patent [19]

Lyons

[11] Patent Number: 5,103,683
[45] Date of Patent: Apr. 14, 1992

[54] ROTARY DRUM SAMPLING DEVICE

[75] Inventor: Richard G. Lyons, Middletown, Ohio

[73] Assignee: Armco Steel Company, L.P., Middletown, Ohio

[21] Appl. No.: 638,920

[22] Filed: Jan. 9, 1991

[51] Int. Cl.⁵ .............................................. G01N 1/00
[52] U.S. Cl. .................................................. 73/863.51
[58] Field of Search ........... 73/863.01, 863.41, 863.42, 73/863.45, 863.51, 863.52, 863.56, 863.57, 863.81, 863.86

[56] References Cited

U.S. PATENT DOCUMENTS

| | | | |
|---|---|---|---|
| 1,063,725 | 6/1913 | Petersen | 73/863.57 |
| 1,423,890 | 11/1922 | Warner | |
| 2,020,529 | 11/1935 | Thorsten | 73/863.57 |
| 3,241,371 | 3/1966 | Horeth | 73/422 |
| 4,574,645 | 3/1986 | Allen et al. | 73/863.51 |

FOREIGN PATENT DOCUMENTS

| | | | |
|---|---|---|---|
| 2425742 | 12/1975 | Fed. Rep. of Germany | 73/863.57 |
| 569894 | 10/1977 | U.S.S.R. | |

OTHER PUBLICATIONS

ISO 3082: 1987(E), FIG. 6.

Primary Examiner—Robert Raevis
Attorney, Agent, or Firm—R. J. Bunyard; L. A. Fillnow; R. H. Johnson

[57] ABSTRACT

A device for systematic sampling coarse material sliding down an inclined chute. A bottom portion of the chute is removed and replaced by a sampling device mounted below the chute opening. The sampling device includes a drum for receiving the sample, a gate mounted to the bottom of the chute for rotation between open and closed positions and a motor for rotating the drum. The outer surface of the drum is provided with an opening. The drum is rotated until the drum opening is aligned with the chute opening causing the gate to be rotated to its open position. Material is diverted from the chute into the drum. After the sample is obtained, rotation of the drum is continued until the gate is closed so that the material continues to slide down the chute without passing into the drum.

5 Claims, 4 Drawing Sheets

ROTARY DRUM SAMPLING DEVICE

BACKGROUND OF THE INVENTION

The invention relates to new and useful improvements in apparatus for sampling free running coarse materials. More particularly, the invention relates to a sampling device for use with an inclined chute.

Materials used in an integrated steel making operation include iron ore, agglomerated iron ore pellets, limestone, coal, coke, sinter and the like. Sampling is required to determine size distribution, chemical composition, physical properties and moisture content. These materials are conventionally sampled using a swinging arm, cutter type, sampling device positioned at the end of a belt conveyor. This type sampling device is cost effective if there is no space limitation. A cutter type sampling device also can be used to cut an entire sample from a moving belt. This device does not have the space limitation but is costly to install and maintain.

Russian patent 569,894 discloses a revolving cylindrical sampling device disposed within a chute for sampling free running materials. The device includes slotted openings for receiving a sample as the material passes through the chute. It also is known to provide an opening in a materials flow chute and to dispose a sampling device within the opening. U.S. Pat. No. 4,574,645 discloses a device for sampling wood chips with the upper end of the sampling device positioned within a vertical feed chute extending through an opening provided in the sidewall of the chute. The device includes an angularly disposed rotatable tube positioned within the chute having its upper end for receiving the sample. The upper end of the tube includes a receptacle and a deflector. When it is desired to take a sample, the tube is rotated until the opening of the receptacle faces upwardly to collect a sample. Otherwise, the tube is rotated with the deflector facing upwardly. U.S. Pat. No. 3,241,371 discloses a device for sampling drill cuttings having a sample receiving end positioned within a drill cuttings flow line extending through an opening provided in the sidewall of the flow line. The sample receiving end of the device includes a flapper valve actuated through a linkage driven by a solenoid. Although these latter sampling devices require minimal space, they are difficult to maintain and/or rapidly become eroded because they are positioned within the materials chute. These materials can be very abrasive and generally disintegrate the sampling device relatively quickly.

Accordingly, there remains a need for a device not subject to space limitations for the systematic sampling of free running abrasive materials. Furthermore, there remains a need for a sampling device which is inexpensive, easy to maintain and has a long life.

BRIEF SUMMARY OF THE INVENTION

The invention relates to a device for systematic sampling of coarse material sliding down an inclined chute. The sampling device includes a receptacle, a gate and means for moving the gate between open and closed positions. The sampling device is mounted beneath an opening provided in the chute. The upper surface of the gate has a configuration such that the material may pass through the chute opening into the receptacle when the gate is in the open position and prevents the material from passing through the chute opening when the gate is in the closed position.

A principal object of the invention is to provide a compact device capable of systematic sampling of coarse material on a time or a mass flow basis.

An additional object includes a sampling device which is not mounted directly within the chute.

The invention relates to a device for sampling coarse material sliding down a chute and includes a receptacle, a gate, means for moving the gate between open and closed positions and the sampling device being mounted beneath an opening provided in the chute so that the material passes through the opening into the receptacle when the gate is in the open position.

Another feature of the invention includes the gate being connected to the chute.

Another feature of the invention includes the gate having a configuration such that the material passes through the chute opening into the receptacle when the gate is in the open position and prevents material from passing through the chute opening when the gate is in the closed position.

Another feature of the invention includes the gate having a bottom surface configuration similar to the outer surface of the receptacle.

Another feature of the invention is for the sampling device to include a motor actuated by a process controller at predetermined time or mass flow intervals to rotate the receptacle for moving the gate between the open and closed positions.

Advantages of the invention include inexpensive installation, reduced maintenance costs, long life expectancy, improved material quality control and minimal operator labor.

BRIEF DESCRIPTION OF THE DRAWINGS

FIG. 3 is a perspective view of the sample receptacle of FIG. 2.

DETAILED DESCRIPTION OF THE PREFERRED EMBODIMENT

The invention relates to a device for systematic sampling abrasive, coarse materials such as sinter, iron ore, coal, coke, limestone and the like while sliding down an inclined chute. These materials may be natural, agglomerated or pelletized and generally have particle sizes at least about 5 mm.

The sampling device is for positioning beneath an opening provided in the chute and external to the material flow within the chute. The device includes a receptacle for receiving a sample, a gate and means for moving the gate between open and closed positions. Material passes from the chute into the receptacle when the gate is moved to the open position.

Figure 1:
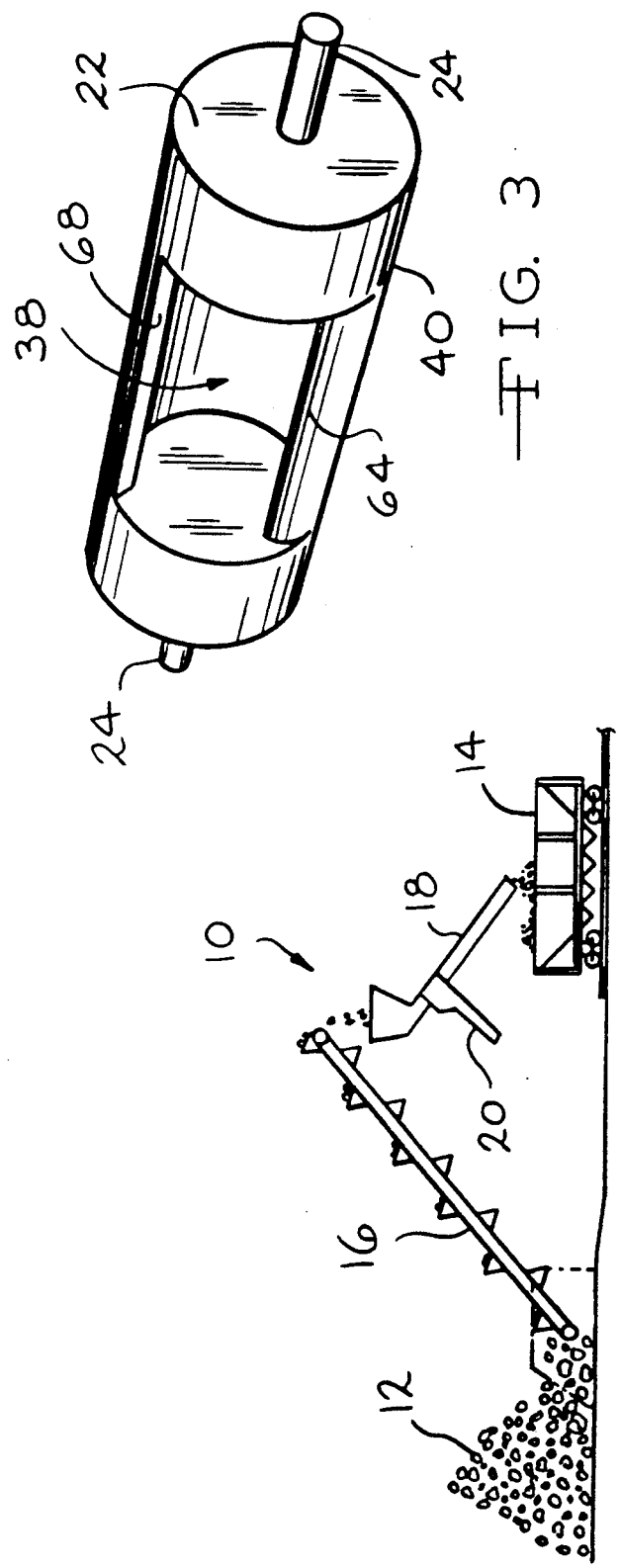
FIG. 1 is a schematic view illustrating use of the invention at a materials handling facility.

The invention will be more fully understood from the following detailed description of a preferred embodiment illustrated in the drawings. Referring to FIG. 1, reference numeral 10 generally illustrates a materials storage facility such as found at the smelting and melting end of a steel plant, a mine, an agglomeration plant or a materials handling facility such as for a loading dock, rail yard and the like. Facility 10 may include any number of stockpiles or storage bins of coarse material 12, transportation equipment 14 to be loaded with the material and conveyances for loading or distributing the coarse material such as a conveyor 16 and a chute 18. A sampling device 20 incorporating the invention is positioned in conjunction with chute 18.

Figure 2:
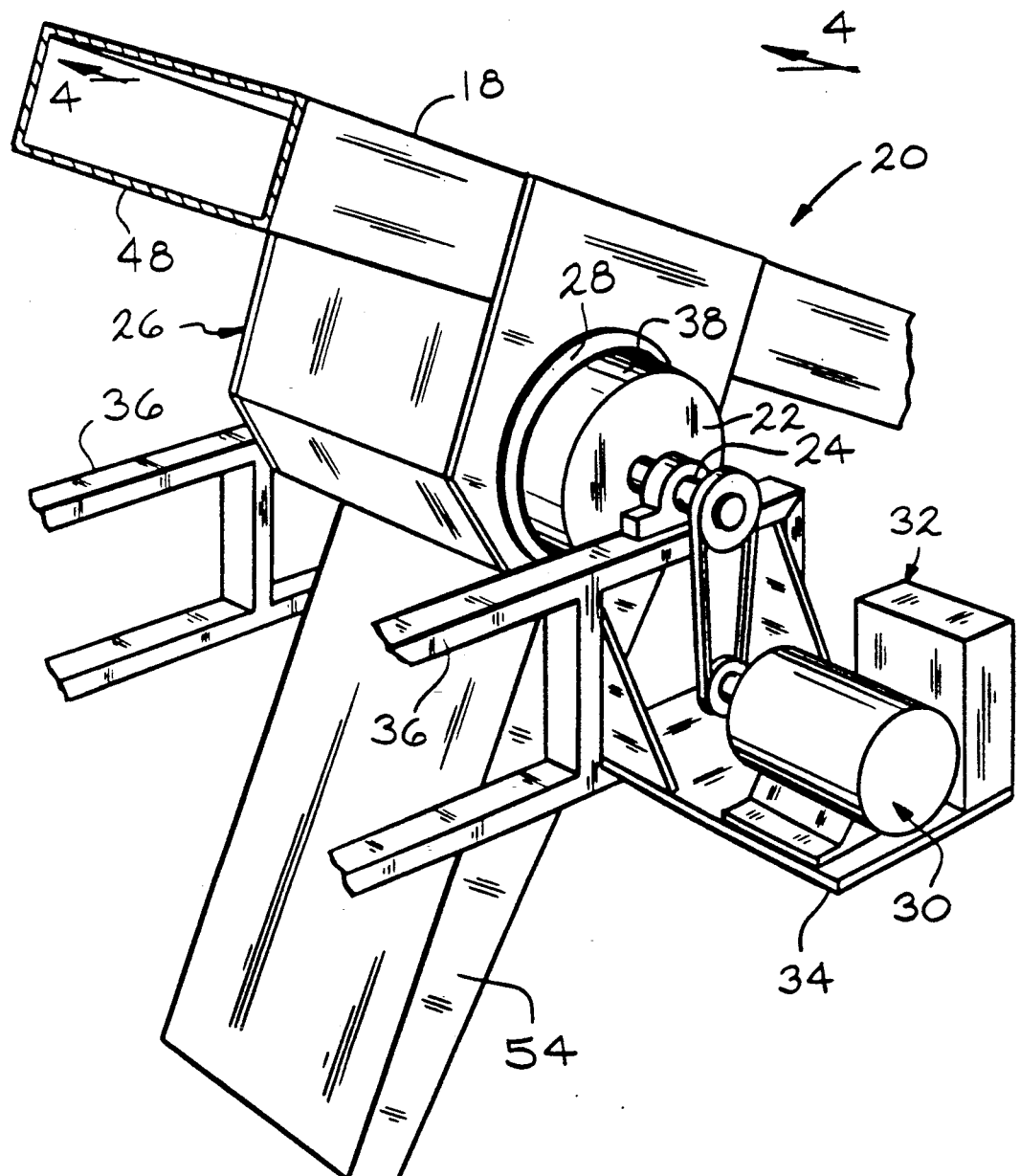
FIG. 2 is a perspective view illustrating one embodiment of the invention.

FIG. 2 illustrates sampling device 20 supported from the bottom side of inclined chute 18 and includes a sample receiving receptacle such as a drum 22 supported on a shaft 24 within a housing 26 connected to chute 18. Each end of housing 26 includes an enclosed bearing assembly 28 for rotationally supporting drum 22. Means for shifting drum 22 between open and closed positions includes an electric motor 30 and a process controller 32, both mounted on a base 34 which is supported by structural members 36. It will be understood configurations other than a cylindrical shape could be used for receptacle 22. It will be further understood means for shifting receptacle 22 could be other than rotational. For example, receptacle 22 could be box shaped and shifted between open and closed positions by sliding.

FIG. 3 illustrates drum 22 removed from sampling device 20. Drum 22 includes an opening 38 extending through its outer surface 40 for passage of a sample into drum 22.

Figure 4:
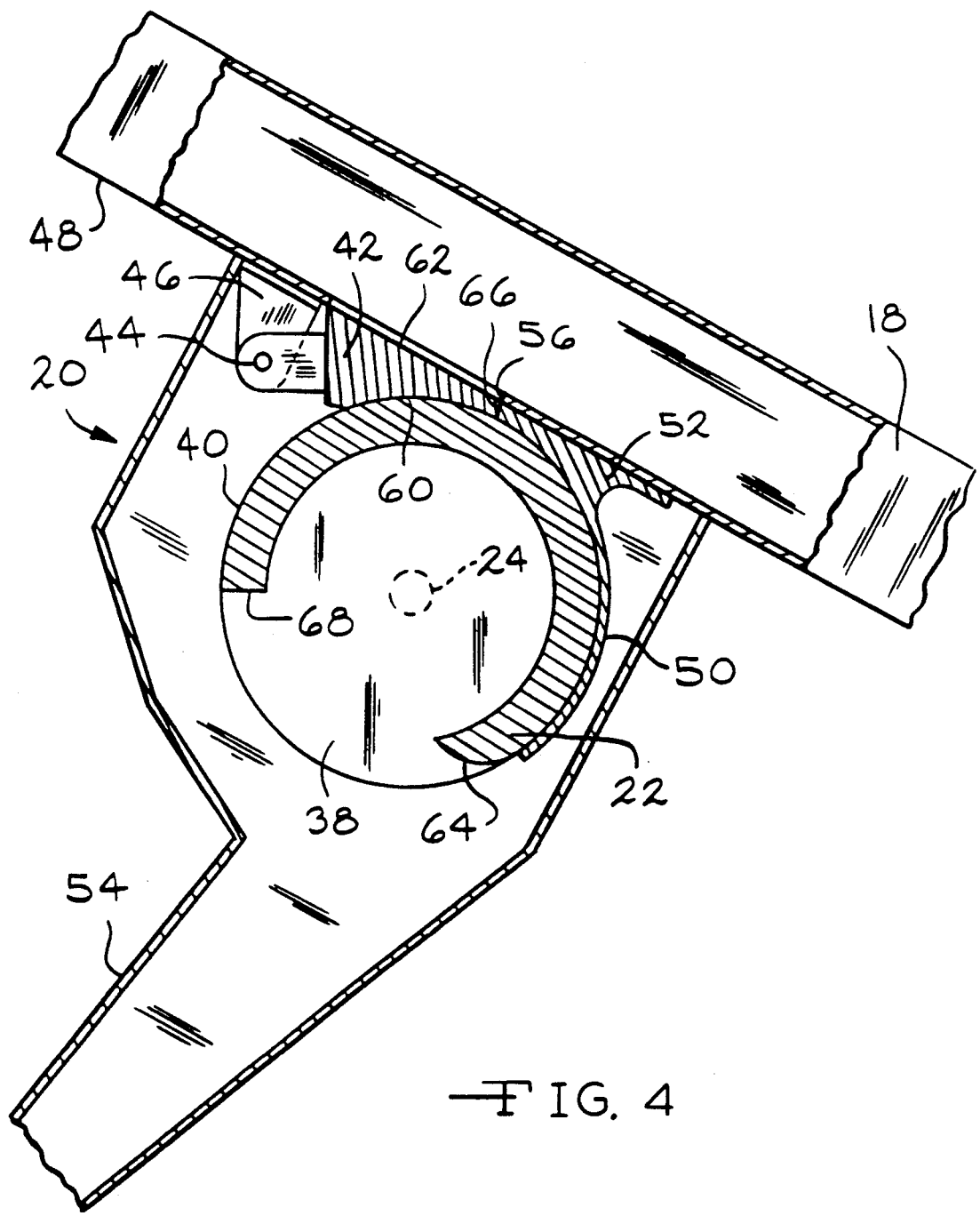
FIG. 4 is a section view along line 4—4 of FIG. 2 illustrating the sampling device in the closed position.

FIG. 4 illustrates in section sampling device 20 taken along line 4—4 of FIG. 2 with certain parts removed with drum 22 being shifted to a closed position. Device 20 further includes a gate 42 mounted on a rod 44 which is journalled in a pair of brackets 46 fixed to the bottom 48 of chute 18. An arcuate plate 50 extends from a bracket 52 connected to bottom 48 of chute 18 and is urged against outer surface 40 of drum 22. Gate 42 is tapered for positioning within the nip formed between outer surface 40 of drum 22 and bottom 48 of chute 18. Bottom surface 60 of gate 42 is configured for intimate contact with outer circular surface 40 of drum 22 and upper surface 62 of gate 42 is flat for intimate contact with the planar surface of bottom 48 of chute 18.

Figure 5:
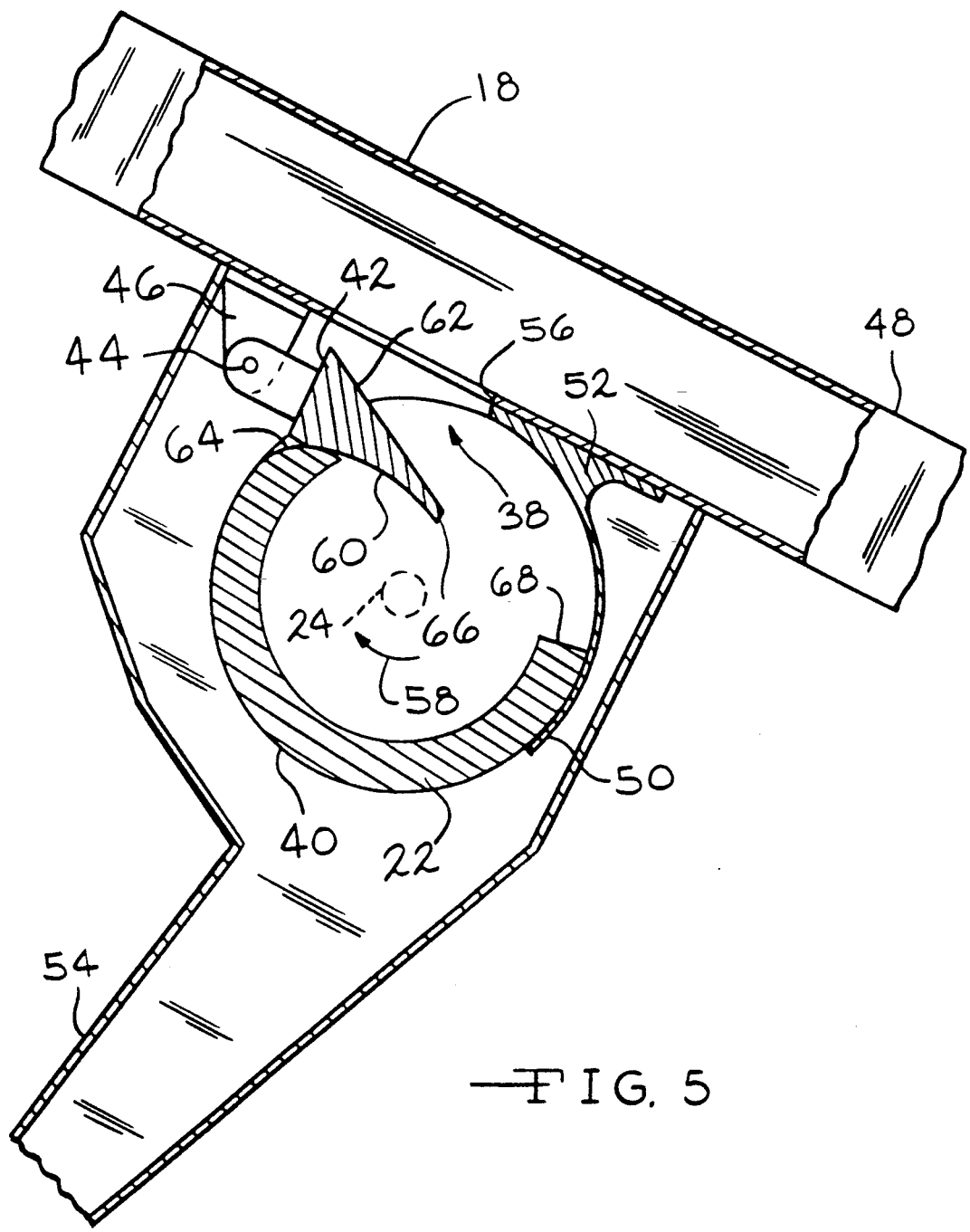
FIG. 5 is a section view similar to that of FIG. 4 illustrating the sampling device in the open position.

FIG. 5 illustrates a view similar to FIG. 4 except drum 22 is shifted to an open position. Drum 22 is rotated clockwise (arrow 58) until opening 38 is shifted to the upper position immediately below an opening 56 in bottom 48 of chute 18. To prevent coarse material from obstructing either of openings 38 or 56, the openings must be at least three times as large as the diameter of the largest anticipated piece of coarse material. As soon as an edge 68 of opening 38 rotates past a terminal end 66 of gate 42, gate 42 drops away from opening 56 and into opening 38 allowing the material to be diverted from chute 18 through opening 56. Bottom 60 of gate 42 is supported by a tapered edge 64 of opening 38 and top surface 62 of gate 42 directs the sample passing through opening 56 into drum 22. After the amount of time needed to accumulate the necessary sample size, clockwise rotation of drum 22 is continued whereby the caming action of tapered edge 64 against arcuate surface 60 rotates gate 42 upwardly to close opening 56. This time may be predetermined based on the known mass flow rate of material sliding down chute 18 or it may be determined by using load sensors to weigh the amount of sample within drum 22. Rotation of drum 22 is continued to the position shown in FIG. 4 with the sample within drum 22 being dumped into a box 54. Plate 50 retains the material within drum 22 until opening 38 is returned approximately to the position shown in FIG. 4.

Operation of device 20 now will be described. Depending upon the quality control requirements necessary for the material, controller 32 is programmed to systematically activate motor 30. The length of time to accumulate the sample during which drum 22 remains in the open position will depend upon the sample size needed, the mass of material traveling per unit of time down the chute and the size of the opening in the chute. At the predetermined time, controller 32 activates motor 30 causing it to rotate drum 22 approximately 180° from the position shown in FIG. 4 to the position shown in FIG. 5. Material then passes through opening 56 in chute 18, through opening 38 in surface 40 and into drum 22. After the predetermined sample size has been obtained, controller 32 again activates motor 30 and rotation of drum 22 is continued back to the position shown in FIG. 4. When opening 38 is rotated to near its bottom position, the sample inside drum 22 is released through opening 38 into box 54. The sample then is ready for further processing or analysis.

It will be understood various modifications can be made to the invention without departing from the spirit and scope of it. For example, brackets 46,52 and edges 64, 68 of opening 38 could be mounted as a mirror image to that illustrated in FIG. 5. Opening 38 then would be shifted by counterclockwise rotation of drum 22. Receptacle 22 also could be box shaped with the upper surface of the receptacle functioning as a gate. The gate would be opened by sliding the box until an opening in the upper surface of the box was aligned with the opening in the chute. Therefore, the limits of the invention should be determined from the appended claims.

What is claimed is:

1. In apparatus for sampling free running coarse materials, comprising:
   an inclined chute having a bottom opening,
   said opening being at least three times as large as the diameter of the largest anticipated piece of the material,
   a sampling device mounted beneath said opening for receiving a sample of the material,
   said sampling device including a drum, a gate rotatably connected to the bottom of said chute and means for systematically rotating said drum thereby moving said gate between open and closed positions,
   the bottom of said gate having a circular configuration for engaging the outer surface of said drum when said gate is in said closed position,
   the upper surface of said gate having a planar configuration for engaging the bottom surface of said chute when said gate is in said closed position for closing said opening.

2. In apparatus for sampling free running coarse materials, comprising:
   an inclined chute having a bottom opening,
   a sampling device mounted beneath said opening for receiving a sample of the material,
   said sampling device including a drum, a gate and means for systematically rotating said drum thereby moving said gate between open and closed positions,
   said drum having an opening for juxtaposition with said chute opening when said gate is in said open position, said openings being at least three times as large as the diameter of the largest anticipated piece of the material, said gate rotatably connected to the bottom of said chute and positioned within a nip formed between said chute and said drum, the bottom of said gate having a circular configuration for engaging the outer surface of said drum when said gate is in said closed position, the upper surface of said gate having a planar configuration for engaging the bottom surface of said chute when said gate is in said closed position for closing said chute opening.

3. In apparatus for sampling free running coarse materials, comprising:

an inclined chute having a bottom opening, said opening being at least three times as large as the diameter of the largest anticipated piece of the material, a sampling device mounted beneath said opening for receiving a sample of the material, said sampling device including a cylindrically shaped receptacle, a gate and means for moving said gate between open and closed positions, said gate being rotatably connected to the bottom of said chute and positioned within a nip formed between said chute and said receptacle, the bottom of said gate having a circular configuration for engaging the outer surface of said receptacle when said gate is in said closed position, the upper surface of said gate having a planar configuration, and said gate for closing said opening when in said closed position.

4. The apparatus of claim 3 wherein said moving means includes a motor.

5. The apparatus of claim 3 wherein said moving means includes a motor and a controller, said controller being programmable at predetermined intervals for systematically activating said motor for moving said gate between said open and closed positions.

* * * * *